United States Patent [19]

Mäkelä et al.

[11] Patent Number: 4,974,459
[45] Date of Patent: Dec. 4, 1990

[54] PROCEDURE FOR IMPLEMENTING SELECTION OF LIQUIDS IN LIQUID DISPENSING IN AN ANALYZER, AND SAMPLING DEVICE

[75] Inventors: Keijo Mäkelä; Pertti Nuopponen; Pertti Tuominen, all of Espoo, Finland

[73] Assignee: Kone Oy, Finland

[21] Appl. No.: 334,292

[22] Filed: Apr. 6, 1989

[30] Foreign Application Priority Data

Apr. 15, 1988 [FI] Finland .............................. FI 881779

[51] Int. Cl.$^5$ .............................................. G01N 1/14
[52] U.S. Cl. ................................ 73/864.081; 436/180
[58] Field of Search ........... 73/864.81, 864.85, 864.87, 73/864.86; 436/180

[56] References Cited

U.S. PATENT DOCUMENTS

| 3,991,626 | 11/1976 | Shair | 73/864,87 X |
| 4,022,065 | 5/1977 | Ramin et al. | 73/846.87 X |
| 4,182,184 | 1/1980 | Bakalyar et al. | 73/864.87 |
| 4,641,541 | 2/1987 | Sharp | 73/864.81 |
| 4,644,807 | 2/1987 | Mar | 73/864.87 X |

Primary Examiner—Tom Noland
Attorney, Agent, or Firm—Lerner, David, Littenberg, Krumholz & Mentlik

[57] ABSTRACT

A procedure for implementing the liquid selection of analyzer liquid dispension, includes the steps of selecting a liquid vessel from among a plurality of such vessels, and taking liquid into the dispensing system for further treatment. The liquid path from the liquid vessel that has been selected is so connected to the dispensing unit that (i) the sealing surfaces constituting the connection do not substantially slide against one another and that (ii) sealing at the connection is accomplished by means of elastic deformation of at least one of the bodies being coupled.

3 Claims, 2 Drawing Sheets

4,974,459

PROCEDURE FOR IMPLEMENTING SELECTION OF LIQUIDS IN LIQUID DISPENSING IN AN ANALYZER, AND SAMPLING DEVICE

BACKGROUND OF THE INVENTION (a) Field of the Invention

The present invention concerns a procedure for implementing selection of liquids in liquid dispensing in an analyzer, involving liquid being taken, from a liquid vessel selected from among a group of several vessels, and introduced into the dispensing system for further treatment.

(b) Description of the Related Art

In analyzers known in the art in which reagent liquids are needed for analysis, reagent liquids are drawn with a needle from open reagent tube-shaped liquid vessels. For each analysis, such reagent vessels must be filled before testing and emptied again after analysis. The reagent liquids are usually stored in a refrigerator. When the analyzer needle is transferred from one vessel to another, so-called cross-pollution may easily occur even if the needle is flushed in the meantime.

SUMMARY OF THE INVENTION

An object of the present invention is to provide a procedure of novel type for implementing liquid dispensing. In the procedure of the invention the liquid path from the liquid vessel selected is connected to the actual dispensing unit in such a manner that the sealing surfaces constituting the connection do not substantially slide against one another, and that sealing at the connection is accomplished by elastic deformation of at least one of the bodies to be connected. According to the invention, the degree of openness of vessels is substantially reduced, whereby evaporation inducing inaccuracy of analysis is also substantially reduced.

Pressure conditions adjacent to the sealing surfaces are arranged to be such that, when the connection is undone, movement of the liquid on the sealing surfaces is inhibited, and the liquid returns to the vessel, all the way from the connection point that has been opened. The capillary forces in the liquid transport path are arranged such that when the connection is opened, the liquid column breaks, forming boundary surfaces which have their borders within the liquid paths.

Furthermore, according to the procedure of the invention, when the communication between the dispensing system and the connection is opened, the pressure conditions are arranged to be such that the liquid moves, all the way from the connection boundary surface, back towards the container, and on the side of the dispensing system, the capillary forces maintain the boundary surface in position without extra efforts prior to change of liquid, the tubular inner surface of the dispensing system is washed. It is therefore an advantage of the system of the invention that no material or influence originating from the solutions, which would be deleterious in view of tightly sealed connection, can reach the sealing surfaces.

The invention also concerns a sampling device for implementing the procedure of the invention. The sampling device consists of a liquid selector comprising a needle by the aid of which, and by the moving of which to the desired target, the requisite liquids can be drawn from the liquid vessel desired in each instance, such as a reagent vessel, to be further analyzed. In the sampling device the dispensing system comprises a needle which conforms to the coupling sockets of the liquid connection.

In an embodiment of the invention the coupling sockets are located on a circle along which the needle can be moved with the aid of a rotating means. This kind of selector circle is easy to manufacture and, the rotating means enables precise selection of the desired coupling socket through which the desired liquid is to be drawn.

In a further embodiment of the invention the coupling sockets consist of an elastic material such as rubber. It is thus understood that the tip of the needle is pressed tight against the coupling socket and no leakage can occur. Furthermore, when the pressure of the needle is made resilient with the aid of a spring force, a constant compressive force is invariably produced between the needle and the coupling socket and wear is substantially reduced.

In a still further embodiment of the invention the port of the coupling socket presents a conical depression, and the tip of the needle has equivalent conical shape. As a consequence, said cones facilitate alignment of the needle with the hole in the coupling socket.

A further embodiment of the invention provides that the coupling sockets communicate by tubing with the liquid vessels, which may be located in storage, for instance, in a refrigerator. Therefore, no separate liquid vessels are required in the analyzer. When the requisite substance is drawn from a liquid vessel, the tube is first filled with liquid, and on termination of suction, the liquid is made to flow back into the liquid vessel in storage.

BRIEF DESCRIPTION OF THE DRAWINGS

Further objects, features and advantages of the invention will become apparent to those skilled in the art from the following description thereof when taken in conjunction with the accompanying drawings in which:

FIG. 2 presents the same embodiment as shown in FIG. 2, but with opened connection with the broken liquid column.

DESCRIPTION OF THE PREFERRED EMBODIMENTS

Figure 1:
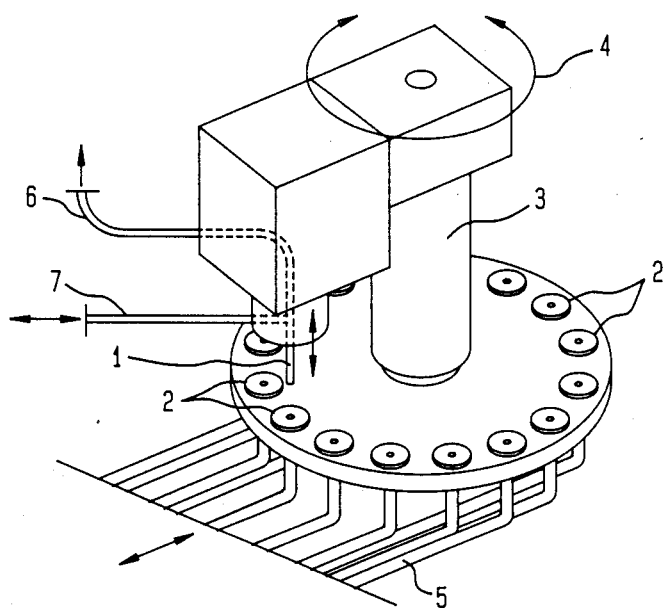
FIG. 1 presents the selector of the present invention in the sampling device of an analyzer, in oblique top view.
Figure 2:
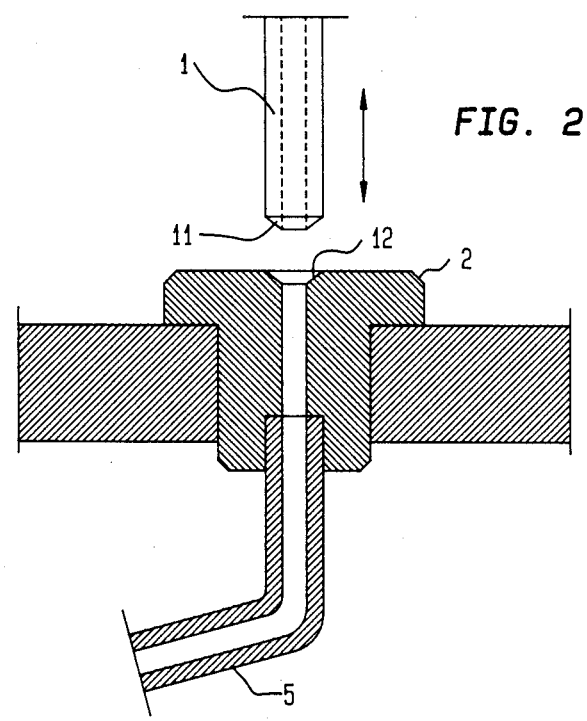
FIG. 2 presents the coupling socket of the present invention, in cross-section, and the needle of the device prior to being coupled.
Figure 3:
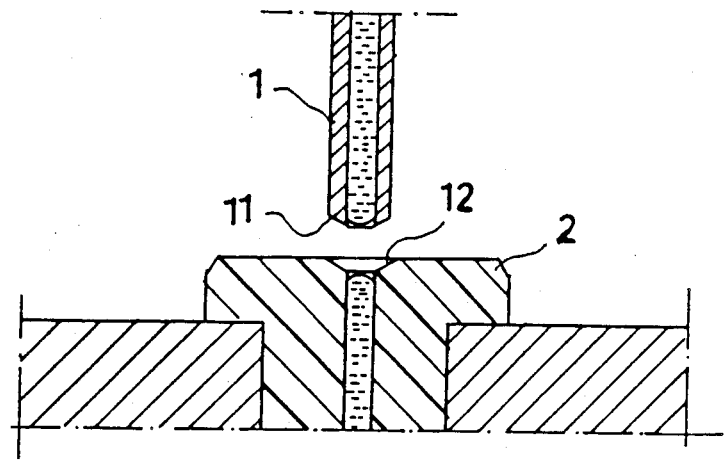

The sampling device of the analyzer consists of a liquid selector comprising a needle 1, by the aid of which and by moving which to the desired point, the reagent liquids required can be drawn from the desired reagent vessel, to be further analyzed. The selector also comprises coupling sockets 2 conforming to the needle 1 and communicating with the reagent vessels, and to which the needle 1 can be connected for taking up the desired liquid. The coupling sockets 2 are located on a circle, on which the needle 1 can be moved with the aid of a rotating means 3 as indicated by arrow 4. The coupling sockets 2 are made of an elastic material such as, for example, rubber. The port of the coupling socket 2 presents a conical depression and the end of the needle 1 has equivalent conical shape as shown in FIG. 2. The coupling sockets 2 communicate by flexible tubes 5 with the reagent vessels, which are located in a storage such as a refrigerator. With the aid of the rotating means 3, the needle is turned into register with the desired socket 2 and the needle is pressed with a given force against the socket, whereby tightly sealed coupling is produced, and the requisite liquid quantity is drawn. The liquid is conducted through the tube 6 to the analyzer, to be further analyzed. Associated with the needle is also another tube 7, with the aid of which e.g. air columns can be created between any two liquid columns that have been drawn. Such air columns may also be employed to separate reagents and/or washing liquids. Air bubble formation in the liquids which are taken up is minimal because there is no step between the port of the needle and the coupling socket. Since the liquids can run freely back to the liquid vessels in the refrigerator, no separate vessels are needed in the analyzer.

It will be obvious to a person skilled in the art that the scope of the invention is not restricted to the embodiments disclosed above, but may instead be varied within the scope of the following claims without departing from the spirit and scope of the invention.

WE CLAIM:

1. A procedure for implementing selection of liquids in liquid dispensing in an analyzer, comprising the steps of removing a liquid from a liquid vessel, selected from among a number of vessels, introducing said liquid into a dispensing system for further treatment and connecting the liquid path from said liquid vessel to a dispensing unit such that sealing surfaces constitute a connection of said liquid path from said liquid vessel to said dispensing unit and do not substantially slide against one another and such that sealing is accomplished in said connection by means of elastic deformation of at least one of a plurality of bodies to be coupled.

2. A procedure according to claim 1, wherein pressure conditions adjacent to said sealing surfaces are such that when said connection is opened, movement of said removed liquid on said sealing surfaces is inhibited and said removed liquid returns to said liquid vessel, all the way from said connection that has been opened.

3. A procedure according to claim 1, wherein capillary forces in said liquid path are such that when said connection is opened, a liquid column between said liquid vessel and said dispensing unit is disrupted, forming a boundary surface of which the borders are within said liquid path.

* * * * *